United States Patent

Huxel et al.

[11] Patent Number: 5,971,987
[45] Date of Patent: Oct. 26, 1999

[54] BIOCOMPATIBLE ABSORBABLE POLYMER FASTENER AND DRIVER FOR USE IN SURGICAL PROCEDURES

[75] Inventors: Shawn T. Huxel, Lakehurst; David W. Overaker, Annandale, both of N.J.

[73] Assignee: Ethicon, Inc., Somerville, N.J.

[21] Appl. No.: 09/157,199

[22] Filed: Sep. 18, 1998

[51] Int. Cl.⁶ .................................................. A61B 17/86
[52] U.S. Cl. ............................ 606/73; 606/72; 606/104; 411/2
[58] Field of Search .................. 606/73, 72, 61, 606/77, 76, 104, 232; 411/2

[56] References Cited

U.S. PATENT DOCUMENTS

| | | | |
|---|---|---|---|
| 2,248,054 | 7/1941 | Becker | 606/104 |
| 3,604,487 | 9/1971 | Gilbert | 606/104 |
| 5,169,400 | 12/1992 | Muhling et al. | 606/73 |
| 5,275,601 | 1/1994 | Gogolewski et al. | 606/72 |
| 5,314,989 | 5/1994 | Kennedy et al. | 528/354 |
| 5,403,347 | 4/1995 | Roby et al. | 606/230 |
| 5,431,679 | 7/1995 | Bennett et al. | 606/230 |
| 5,470,334 | 11/1995 | Ross et al. | 606/72 |
| 5,502,159 | 3/1996 | Liu et al. | 528/354 |
| 5,653,710 | 8/1997 | Harle | 606/73 |
| 5,695,497 | 12/1997 | Stahelin | 606/73 |
| 5,827,287 | 10/1998 | Tunc | 606/77 |

*Primary Examiner*—Michael Buiz
*Assistant Examiner*—David O. Reip
*Attorney, Agent, or Firm*—Hal Brent Woodrow

[57] ABSTRACT

A biocompatible fastener that may be used for attachment of a fixation plate to bone is described herein, where the fastener has features that facilitate its deployment in a surgical environment. The fastener is composed of a screw, having a threaded shaft and slotted head, and a detachable body that is used for deploying the screw and is then broken away and discarded. The slot in the head of the screw has stress concentrating notch features that direct the fracture lines into the screw head upon detachment of the secondary body, thus ensuring that the screw head surface remains smooth after deployment. A suitable driver for applying the fastener is also described.

10 Claims, 4 Drawing Sheets

BIOCOMPATIBLE ABSORBABLE POLYMER FASTENER AND DRIVER FOR USE IN SURGICAL PROCEDURES

FIELD OF THE INVENTION

The field of art to which this invention relates is surgical devices, in particular absorbable orthopaedic fasteners. Specifically, absorbable polymer screws for use in the fixation of bone and cartilage, especially hard tissue of the cranium, face and other plastic/reconstructive procedures.

BACKGROUND OF THE INVENTION

There are currently a variety of metallic screws available for attaching bone plates to fracture and surgery repair sites; spinal, cranial, and maxillo-facial plates have all been fastened using metal screws. The disadvantage of metal devices is that they are permanent and must be removed through a second surgical procedure. If they remain in the body, tissue atrophy and subsequent loosening of the screw may occur. Synthetic absorbable biocompatible polymers are well known in the art. Such polymers are typically used to manufacture medical devices, which are implanted in body tissue and absorb over time. Synthetic absorbable biocompatible aliphatic polyesters include homopolymers, copolymers (random, block, segmented and graft) of monomers such as glycolic acid, glycolide (d, l, meso and mixtures thereof), lactic acid, lactide, ε-caprolactone, trimethylene carbonate and p-dioxanone. Numerous U.S. Pat. Nos. describe these polymers including 5,431,679; 5,403,347; 5,314,989; 5,431,679; 5,403,347; and 5,502,159.

With the advent of absorbable polymers has come a new generation of fasteners (screws, pins, etc.) that are designed to be gradually absorbed by the body as their functional use declines. Screws made of an absorbable material have an advantage in that they remain only for the period of time required for healing. There are a number of threaded fasteners disclosed in the prior art which utilize absorbable materials.

U.S. Pat. No. 5,169,400, hereinafter Muhling et al., discloses a bone screw made of resorbing plastic material comprising an internal tool insertion channel that is coaxial with the screw shaft and extends along most of the length of the shaft, where the cross-section of the insertion channel is non-circular and matches the cross-section of the insertion tool.

U.S. Pat. No. 5,470,334, hereinafter Ross et al., discloses a bioabsorbable interference bone fixation screw having an internal coaxial channel into which a rotatable driver may be inserted for screw application. The channel defines a number of radial forces receiving surfaces for transmitting forces from the driver to the screw.

U.S Pat. No. 5,695,497, hereinafter Stahelin, discloses a biodegradable screw and suitable screwdriver. The screw consists of an internal coaxial channel, with a plurality of lobe areas arranged uniformly about the channel area, which is radially symmetrical about the longitudinal axis in regular rotary steps.

All of these patents relate to screws having an internal coaxial channel that is used for insertion of the device. The disadvantage of having an internal coaxial channel becomes evident when considering a screw with a shaft diameter of 1–2 millimeters or less. Including an internal channel in such a small fastener would leave little remaining material, thus greatly compromising the strength of the device. Such a design is therefore not desirable when the goal is to maximize the strength of a very small threaded fastener, such as would be required in cranio-facial surgical applications where small plates and fasteners are used. However, a very small fastener without an internal channel is difficult to handle during a surgical procedure. A feature is therefore required that will enable the surgeon to grasp and deploy the fastener with ease.

What is needed in this art is a novel solid threaded fastener consisting of an integral component that is used for inserting the fastener and is then detached and discarded while also providing the surgeon means to remove the screw if repositioning is required. The current invention discloses such a device, and an instrument for deploying such a device.

SUMMARY OF THE INVENTION

The invention disclosed is a fastener made of bioabsorbable material comprising a screw composed of an externally threaded shaft and slotted head and a detachable body that extends from the upper surface of the slotted head. The detachable body is used to apply the screw and is then detached and discarded. The detachable body has surface features that allow it to mechanically engage a driver in such a way that the driver may rotate the fastener about its longitudinal axis thereby facilitating the insertion of the screw portion of the fastener into bone tissue. Preferably, stress concentrating notches will be located on the lateral walls of the slot in the screw head in order to direct the failure at the junction of the detachable body and the slotted head such that the slotted head surface remains flush after detachment.

Also disclosed is a driver for placing the bioabsorbable screw. The driver has a channeled end feature which mates with the detachable body of the fastener such that the detachable body may be engaged and then released by the driver. The driver also consists of an internal its plunger that is aligned with the axis of the driver and is used to eject the detachable body of the fastener after it has been applied.

There are a number of advantages of the disclosed design, particularly for a very small screw. The detachable body allows for very stable handling of the fastener during alignment and deployment, while also providing a means of transmitting an adequate amount of torque to the screw shaft for deployment. The notches on the lateral walls of the screw slot ensure that the fracture line after detachment does not extend above the surface of the head. Finally, the slot in the head allows for removal of the screw after detachment if necessary.

The foregoing and other features and advantages of the invention will become more apparent from the following description and accompanying examples.

DETAILED DESCRIPTION OF THE INVENTION

Figure 1:
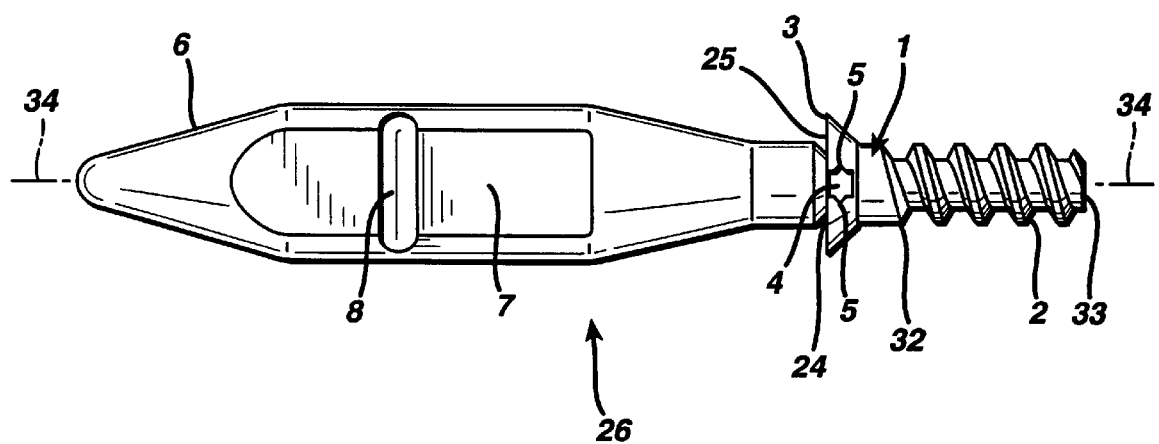
FIG. 1 illustrate the biocompatible, absorbable fastener

The present invention discloses a fastener (26) made of bioabsorbable material having a central axis (34) comprising a screw (1) composed of an externally threaded shaft (2) having a proximal end (32), a distal end (33) and screw head (3) attached to the proximal end (32) with a slot (4), and a detachable body (6) that extends from the upper surface (25) of the screw head (3). The detachable body (6) is used to apply the screw and is then detached and discarded.

Stress-concentrating notches (5) are located on the lateral walls of the slot (4) in the screw head (3) in order to direct the failure at the junction (24) of the detachable body (6) and the screw head (3) such that the yield stress at the upper surface of the screw head remains flush after detachment.

The screw (1) is the fastening component which, when threaded into a passage (hole) in bone, can be used to secure a bone plate or other fixation or surgical device in place. The slot (4) in the screw head (3) is used to remove the screw after deployment if necessary.

The detachable body (6) has features that allow it to mate with a driver (28) in such a way that the driver has the mechanical ability to rotate the screw about its longitudinal axis thereby advancing the screw into a predrilled hole. The cross-section of the detachable body (6) preferably has one or more surfaces (7) parallel to the axial direction of the screw which mate with a channeled end (9) in the driver (28). Alternatively, the detachable body could have protruding surfaces or recesses to provide appropriate mating surfaces to engage (i.e., be formed in a t-shape).

Slots (8) on the surfaces (7) that are perpendicular to the axial may be provided for positive mechanical engagement with a driver (28).

A desirable design feature of the disclosed fastener system is that the junction (24) between the screw (1) and the detachable body (6) must be the structurally weakest point under a torsional load directed along the longitudinal axis of the fastener, the type of load to which the system would be subjected during deployment and detachment of the detachable body (6). This requirement dictates that the yield stress at the junction (24) between the screw (1) and the detachable body (2) will be lower than, or at most equal to, the yield stress of the externally threaded shaft (2) under a given torque load. Stress is defined as a load distributed over an area. This requirement ensures that, under torque loading, the detachable body (6) will detach from the screw (1) at the same time or earlier than failure of the threaded shaft (2) of the screw (1) can occur. In the preferred embodiment, the cross-sectional area of material attachment at the junction (24) between the screw (1) and detachable body (6) is smaller than, or at most equal to, the smallest cross-sectional area, the root diameter, of the externally threaded shaft (3) of the screw (1) to ensure that failure occurs at the junction (24) first.

Sharp corners or notches in load bearing components are areas of high stress. The stress concentration factor is the ratio of the maximum stress at a notch to the stress that would be encountered if no notch were present; it is the magnification factor for stress at the notch. A very sharp, or small radius, notch can produce a very high stress concentration factor, depending on the type of loading and the overall geometry of the component. Notches (5) in the slot (4) in the head (3) of the screw (1) will serve to magnify the stresses just below the junction (24) between the screw (1) and the detachable body (6). Since material failure initiates at points of high stress, the notches (5) serve to direct the fracture line towards the screw (1) and into the head (3).

Directing the fracture line towards the screw (1) is critical in plastic reconstructive procedures, since the surgeon needs to fasten tissue securely without causing undue tissue irritation from burrs left behind from the detachment of the detachable body (6).

Figure 2:
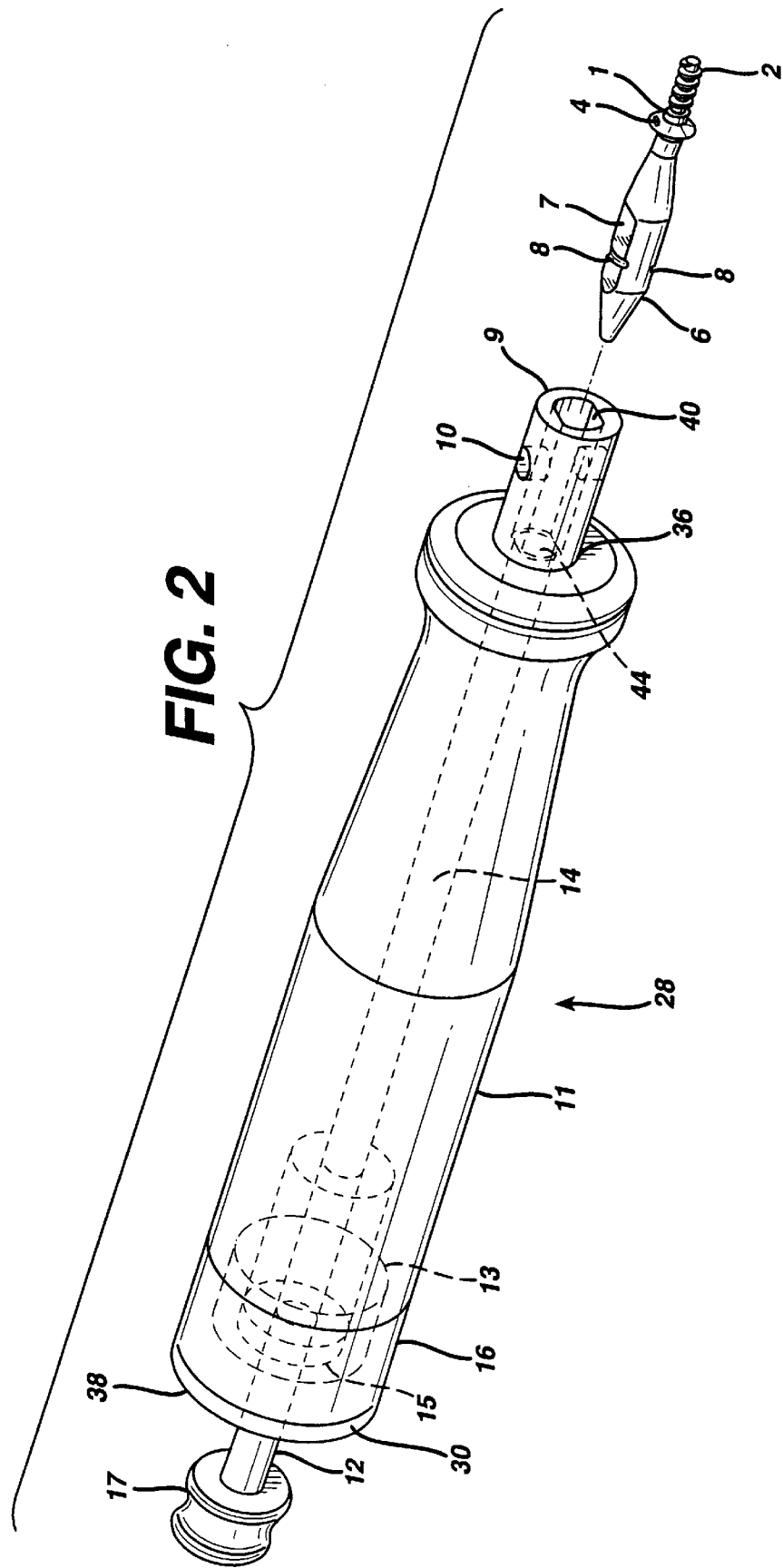
FIG. 2 is a perspective view of the fastener and driver of the present invention.

Also disclosed is a driver (28) for applying the bioabsorbable fastener (26), which is illustrated in FIG. 2. The driver (28) has a receiver (9) that has an internal passage (40) which mates with the detachable body (6) of the fastener (26) such that the detachable body of the fastener may be engaged and then released by the driver. Spring loaded ball bearings or other alignment or locating devices would be placed in the locating channel (10) substantially perpendicular to the axis of the receiver (9) to provide positive engagement with the groove (8) on the flat surfaces (7) of the detachable body (6) of the fastener (26). The driver handle (11) preferably will have a means for ejecting the detachable body (6) of the fastener (26) from the receiver (9). Preferably this means for ejecting the detachable body will be plunger knob (17) which is in mechanical communications with the internal passage (40) of the receiver (9). One preferred embodiment of this invention utilizes a plunger (12) that extends through channel (14) in driver handle (11). The channel (14) is axially aligned and extends through handle (11), through which a plunger (12) travels and the tip (44) of the plunger is used to eject the detachable body (6) of the fastener after the screw (1) is deployed. Concentric with and wider than the channel (14) and traversing only 20 a portion of the total length of the driver handle (11) is a stopper channel (13) through which the stopper (13) of the plunger (12) travels. Located within the stopper channel (13) would be a biasing means, such as a spring (not illustrated), which would resist the forward motion of the plunger (12) and serve to return the plunger to its initial position after screw deployment and detachment. An end cap (30) is fastened to the end of the driver handle (11) to limit the upward travel of the stopper (15) of the plunger (12). The plunger (12) is driven forward by depressing the plunger knob (17).

Figure 3:
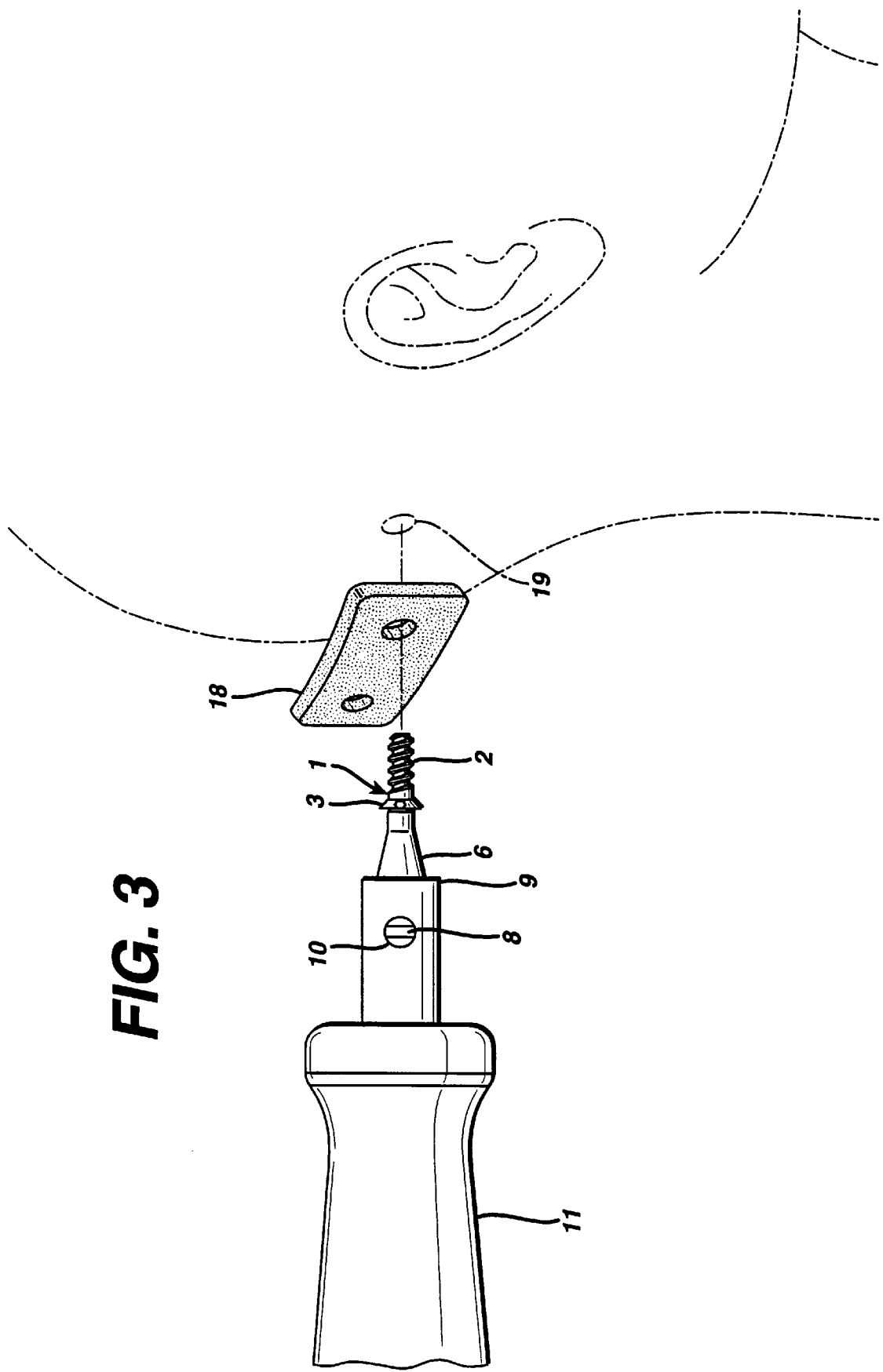
FIG. 3 illustrates the inventive fastener placed within the driver aligned with a predrilled passage (hole) in the patient's cranium.
Figure 4:
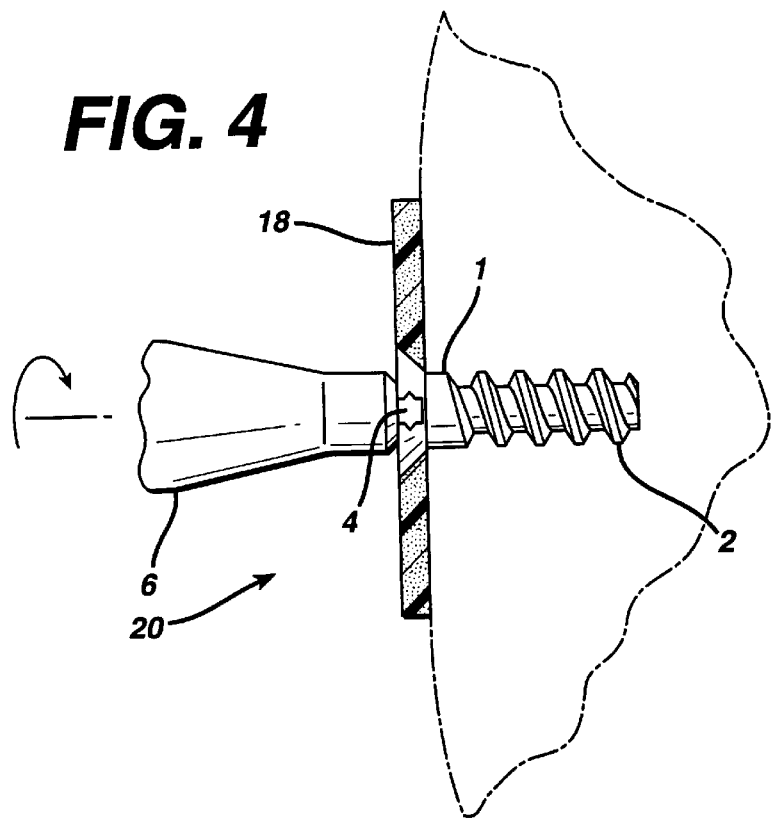
FIG. 4 illustrates the placement of the externally threaded shaft of the fastener within the predrilled hole to secure a bone plate in place.
Figure 5:
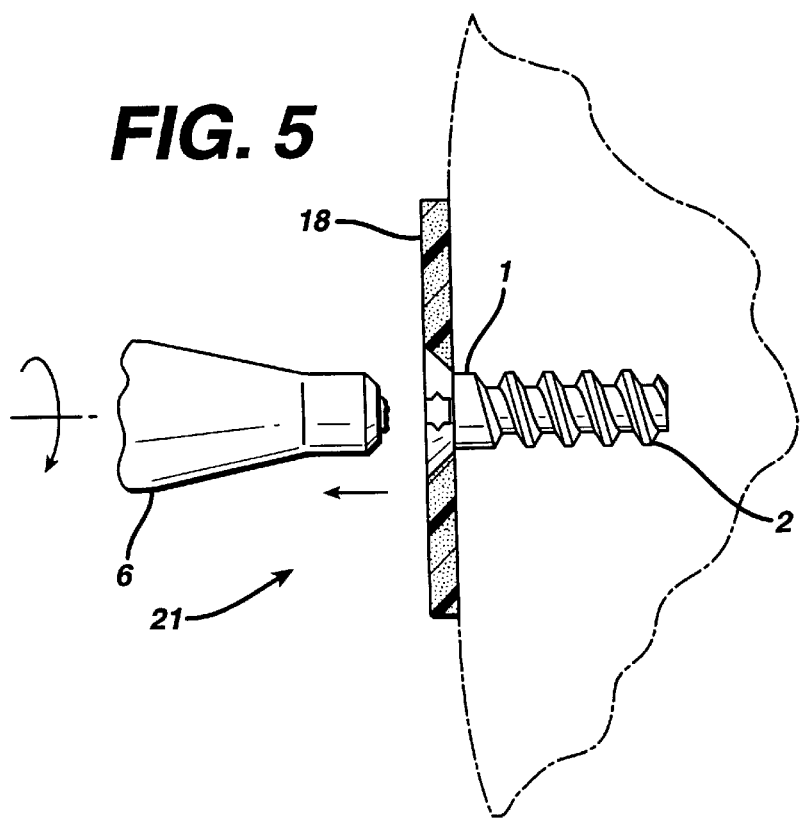
FIG. 5 illustrates the detachment of the detachable body of the fastener from the screw 1.

Also disclosed is a method of applying the fastener as shown in FIGS. 3, 4, and 5. After the surgeon has drilled and tapped a passage (hole) in the bone location where a plate (18) or other device must be fastened, the fastener (26) is removed from the tray by engaging the detachable body (16) of the fastener into the receiver (9). The surgeon then places the screw (1) in the hole and rotates the fastener (26) about its axis (34) to advance the screw into the passage (19). When the screw (1) is fully deployed (20), the surgeon then twists the driver handle (11) further, causing the detachable body (6) to separate from the screw (1) at junction (24).

The surgeon then withdraws the driver handle (23), with the detachable body still engaged, and deploys the plunger to eject the detachable body (24). The process is repeated as needed.

Suitable materials from which the fastener may be formed include biocompatible polymer selected from the group consisting of: aliphatic polyesters; polyorthoesters; polyanhydrides; polycarbonates; polyurethanes; polyamides; polyalkylene oxides; and combinations thereof. The orthopedic fastener of the present invention can also be formed from absorbable glasses or ceramics comprising calcium phosphates and other biocompatible metal oxides (i.e., $C_aO$). The fastener of the present invention can further comprise combinations of absorbable ceramics, glasses and polymers.

In a preferred embodiment, the orthopedic fastener will be formed from an aliphatic polyester(s) and blends thereof. The aliphatic polyesters are typically synthesized in a ring opening polymerization. Suitable monomers include but are not limited to lactic acid, lactide (including L-, D-, meso and D,L mixtures), glycolic acid, glycolide, ε-caprolactone, p-dioxanone (1,4-dioxan-2-one), trimethylene carbonate, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers are generally polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

The polymer blends of the present invention are manufactured in a conventional manner, preferably in the following manner. The homopolymers and copolymers, prepared as described above, are individually charged into a conventional mixing vessel or reactor vessel having a conventional mixing device mounted therein, such as an impeller or equivalents thereof. Then, the polymers and copolymers are mixed at a temperature of about 100° C. to about 230° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes.

Under the above described conditions, the polymers and blends composed of glycolide, ε-caprolactone, p-dioxanone, lactide and trimethylene carbonate will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole.

These molecular weights provide an inherent viscosity between about 0.5 to about 4.0 deciliters per gram (dL/g), more typically about 0.7 to about 3.5 dL/g, and most preferably about 1.0 to about 3.0 dL/g as measured in a 0.1 g/dL solution of hexafluoroisopropanol (HFIP) at 25° C. Also, it should be noted that under the above-described conditions, the residual monomer content would be less than about 5 weight percent.

The absorbable fastener of the present invention are molded from the polymers and blends of the present invention by use of various injection and extrusion molding equipment equipped with dry nitrogen atmospheric chamber(s) at temperatures ranging from about 100° C. to about 230° C., more preferably 140° C. to about 200° C., with residence times of about 1 to about 20 minutes, more preferably about 2 to about 10 minutes. The fastener after molding will be sterilized by conventional means and packaged in an appropriate container for use in a surgical setting.

In another embodiment of the present invention, the polymers and blends can also contain a pharmaceutically active compound or therapeutic agent. The variety of different therapeutic agents that can be used in conjunction with the polymers of the present invention is vast. In general, therapeutic agents which may be administered via the pharmaceutical compositions of the invention include, without limitation: anti-infectives such as antibiotics and antiviral agents; analgesics and analgesic combinations; antiinflammatory agents; hormones such as steroids; bone regenerating growth factors; and naturally derived or genetically engineered proteins, polysaccharides, glycoproteins, or lipoproteins.

The polymers from which the feature is formed may be mixed with the therapeutic agent to form a matrix. The therapeutic agent, may be present as a liquid, a finely divided solid, or any other appropriate physical form.

Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 20%, most typically about 0.001% to about 10% by weight of the matrix. The quantity and type of therapeutic agent incorporated into the matrix will vary depending on the release profile desired and the amount of drug employed.

Upon contact with body fluids, the polymer from which the fastener is formed of, undergoes gradual degradation (mainly through hydrolysis) with concomitant release of the therapeutic agent for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

In another embodiment of the present screw invention, a biocompatible dye could be added to the polymer comprising the device during processing in order to make it more visible in the surgical field.

The following non-limiting examples are illustrative of the principles and practice of this invention. Numerous additional embodiments within the scope and spirit of the invention will become apparent to those skilled in the art.

EXAMPLES

The examples describe a fastener system that is fabricated from an absorbable polymer or polymer blends and is composed of a screw and a detachable body that is used for insertion.

In the synthesis process, the high molecular weight aliphatic polyesters of the device of the present invention are prepared by a method consisting of reacting lactone monomers via a ring opening polymerization at temperatures of 100° C. to 230° C. for 2 to 24 hours under an inert nitrogen atmosphere until the desired molecular weight and viscosity are achieved.

The polymer blends of the present invention are prepared by individually charging the synthesized aliphatic homoand co-polyesters into a conventional mixing vessel. The homopolymers and copolymers are mixed at a temperature of 100° C. to 230° C., for 5 to 90 minutes until a uniformly dispersed polymer blend is obtained.

In the examples which follow, the blends, polymers and monomers were characterized for chemical composition and purity (NMR, FT-IR), thermal analysis (DSC), melt rheology (melt stability and viscosity), molecular weight (inherent viscosity), and baseline mechanical properties (Instron stress/strain).

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Several examples will be described in the following few pages. Parts and percentages where used are parts and percentages as specified as weight or moles.

EXAMPLE 1

Synthesis of a 85:15 (mol/mol) poly(lactide-co-glycolide) copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 268 grams (1.86 moles) of L(-) lactide, 38.4 grams (0.330 moles) of glycolide, 0.53 grams ($7\times10^{-3}$ moles) of glycolic acid initiator, and 131 microliters of a 0.33 M solution of stannous octoate catalyst are added.

The assembly is then placed in a high temperature oil bath at 185° C. The stirred monomers quickly begin to melt. The low viscosity melt quickly increases in viscosity. Mechanical stirring of the high viscosity melt is continued for a total reaction time of 4 hours.

The 85:15 (mol/mol) poly(lactide-co-glycolide) copolymer is removed from the bath, cooled to room temperature under a stream of nitrogen, isolated and ground. The polymer is then dried under vacuum at 110° C. for 24 hours. Inherent viscosity using HFIP as a solvent is 1.90 dL/g.

EXAMPLE 2

Injection molding a screw of an 85:15 poly(lactide-co-glycolide) copolymer 1.5 Kg of the copolymer as formed in Example 2 was added to a nitrogen purged hopper of a 28 ton Engel injection molder equipped with an 18 mm diameter barrel to form a screw fastener as shown in FIGS. 1-2. Three heating zones of 200, 190, and 185° C. were employed to melt the blend as it entered the barrel. A nozzle temperature of 185° C. with an injection pressure of 700 psi and a speed of 2 in/s were used to feed the molten material down the barrel. Each injection produced a single part in a single cavity mold. A temperature of 45° C. was used in the mold to optimize the stress levels in the part. Using this process 2 parts are formed per minute.

EXAMPLE 3

Step-by-step process of tool and screw use.

Referring to FIGS. 3, 4, and 5; after the surgeon has drilled and tapped a hole (19) in the bone location where a plate (18) or other device must be fastened, the screw (1) is lifted from the tray by inserting the channeled end of the driver onto the detachable body of the fastener. The surgeon then places the screw in the hole and torques it down into the hole. When the screw is fully deployed (See FIG. 4), the surgeon then twists the driver handle further (See FIG. 5), causing the detachable body to detach from the screw. The surgeon then deploys the plunger to eject the detachable body. The process is repeated as needed.

Alternatively, the fastener could be applied by hand.

We claim:

1. A surgical fastener made of a bioabsorbable polymer comprising a screw having an externally threaded shaft with a proximal end;

a screw head attached to the proximal end of the screw shaft, the screw head having an upper surface which has a slot; and a detachable body extending from the upper surface of the screw head, the detachable body being detachably linked to the screw head;

wherein present in the slot is at least one stress concentration notch to facilitate the separation of the detachable body from the upper surface of the screw head.

2. The surgical fastener of claim 1 wherein the biocompatable fastener is made from biocompatible aliphatic polyesters.

3. The surgical fastener of claim 2 wherein the aliphatic polyester is formed from a monomer selected from the group consisting of lactic acid, lactide (including L-, D-, meso and D,L mixtures), glycolic acid, glycolide, ε-caprolactone, p-dioxanone (1,4-dioxan-2-one), trimethylene carbonate, 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

4. The surgical fastener of claim 1 wherein the detachable body has a central axis and an external surface that facilitates the mating of the detachable body with a device for rotating the body about its axis.

5. The surgical fastener of claim 4 wherein the external surface of the detachable body has one or more flat surfaces.

6. The surgical fastener of claim 4 wherein the detachable body is linked to the screw head at a junction that is the weakest point under a torsional load directed along the axis of the fastener.

7. A fastener and driver combination comprising:

a fastener made of bioabsorbable material comprising a screw having an externally threaded shaft with a proximal end and a screw head attached to the proximal end of the screw shaft, the screw head having an upper surface which has a slot, extending from the upper surface of the screw head is a detachable body, the detachable body being detachably linked to the screw head at a junction and having an external surface; and a driver having a handle with a proximal and distal end, the distal end of the handle being attached to a receiver having an internal passage that has a suitable size and shape to engage the external surface of the detachable body of the fastener and a means for releasing the detachable body of the fastener;

wherein the means for releasing the detachable body is a plunger that ejects the detachable body from the receiver.

8. The fastener and driver combination of claim 7 wherein the external surface of the detachable body has a flat surface which may be used for positive mechanical engagement of the detachable body into said driver.

9. The fastener and driver combination of claim 7 wherein the driver has a plunger knob on the proximal end of the driver body that is in mechanical communications with a plunger tip that can contact and eject the detachable body.

10. The fastener and driver combination of claim 9 wherein the driver handle has a central channel extending from the proximal to the distal end of the driver handle and a plunger extends from the plunger knob through the channel to the plunger tip to provide mechanical communications between the plunger knob and the plunger tip to eject the detachable body from the receiver.

* * * * *